United States Patent

Anderson et al.

[11] Patent Number: 5,846,569
[45] Date of Patent: Dec. 8, 1998

[54] COLOSTRUM SUPPLEMENT

[75] Inventors: Michael R. Anderson, Boca Raton, Fla.; Stephen R. Krauss, San Luis Obispo, Calif.

[73] Assignee: Creative Labs, Inc., Boca Raton, Fla.

[21] Appl. No.: 879,954

[22] Filed: Jun. 20, 1997

[51] Int. Cl.$^6$ ............................. A61K 35/20; A23L 1/30
[52] U.S. Cl. ....................... 424/535; 424/474; 424/157.1; 426/648; 426/580
[58] Field of Search .................................... 424/474, 535, 424/157.1; 426/648, 580

[56] References Cited

U.S. PATENT DOCUMENTS

| | | | |
|---|---|---|---|
| 4,051,235 | 9/1977 | Plymate | 424/157.1 |
| 5,143,848 | 9/1992 | Scholten et al. | 436/8 |
| 5,500,229 | 3/1996 | Aalto et al. | 424/535 |

*Primary Examiner*—Leon B. Lankford, Jr.
*Assistant Examiner*—Christopher R. Tate
*Attorney, Agent, or Firm*—Beehler & Pavitt

[57] ABSTRACT

A consumable supplement contains a colostrum component composed of processed bovine colostrum, magnesium peroxide as a source of active oxygen, a vitamin such as vitamin C, magnesium succinate and a bioflavonoid. This colostrum component can be taken separately or admixed with other minerals, vitamins and the like. In one form, the colostrum component is used as an outer shell for a composite pill, tablet or capsule which includes an inner core containing one or more vitamins, minerals, enzymes or omega acids in the event that the components of the inner core are incompatible with one or more materials of the colostrum component. In this way, a wide variety of supplements may be provided offering the advantages of colostrum and active oxygen and the advantages of other materials which may be taken as a single pill or capsule. Various supplements and formulations are described as well as various amounts of the varius components of the supplement.

10 Claims, No Drawings

COLOSTRUM SUPPLEMENT

RELATED APPLICATIONS

Reference is made to application Ser. No. 08/863,419, filed on May 27, 1997 and assigned to the same assignee.

FIELD OF THE INVENTION

This invention relates to consumable products containing colostrum, more particularly to improved vitamin and mineral supplements and related products which contain activated oxygen and which include colostrum, both in solid form, and which provide many advantages as well as beneficial effects as dietary supplements, improved metabolic function and rapid adsorption into the body.

BACKGROUND OF THE INVENTION

Colostrum is a lactation product produced by the mother after birth (parturition) of mammals such as humans and cows. It is reported and recognized that the nursing newborn receives antibodies from the mother and which are present in colostrum during early feeding after birth Blanc, B., 1981; Biochemical aspects of human milk-comparison with bovine milk; World Rev. Nutr. Diet. 36:1–89. Typically, the term colostrum milk is used to designate the mammal milk produced for about 5 to 7 days after parturition. Colostrum is yellow in color since the concentration of catenoids is high, as much as ten times that of mature milk (that produced about 21–22 days after parturition). It is also known that colostrum has higher protein and mineral content as compared to mature milk: it is also lower in fat and lactose content than mature milk.

It is reported (Blanc, supra) that the percentage of protein in bovine colostrum is about twice that of human colostrum. This source of natural protein is an attractive aspect of colostrum or products made from colostrum. Further, bovine colostrum contains about 50% of a somatic cell known as polymorphonuclear leukocytes. Human colostrum contains mainly mononuclear leukocytes.

Medical researchers have been attracted to colostrum because of the immunological aspects. Colostrum is known to contain a number of leukocytes, immunoglobulins and lysozymes The typical immunoglobulins include IgA, IgD, IgE, IgG and IgM, with IgG being the most abundant. The literature also reports that the immunological effect of colostrum milk is reduced due to the hostile character of the stomach, see: Roos et al, 1995, "15N-labeled immunoglobulins from bovine colostrum are partially resistant to digestion in human intestine", Journal of Nutrition, 125(5): 1238–44, May. Earlier, it had been reported that the main antibody in milk, lgA, functions on mucosal membranes such as the mouth, throat, nasal, lungs, eyes, rectum etc. to prevent infection from the outside, see: Hanson, Lars A. et al, '1998, "Antiviral and Antibacterial Factors in Human milk", in Lars A. Hanson, ed. Biology of Human Milk, Nestle Nutrition Workshop Series, Vol. 15, Raven Press, New York. Thus, colostrum is recognized as having antibacterial activity, in part due to the presence of lactoferrin in bovine colostrum, see U.S. Pat. No. 4,342,747. Also present in colostrum are enzymes such as lactoperoxidasethiocyanate plus peroxidase and xanthine oxidase which oxidize bacteria by generating and releasing hydrogen peroxide.

While colostrum has some antibacterial properties, those properties can be enhanced naturally by incorporation of a source of oxygen into any colostrum product intended for consumption by ingestion. The provision of active oxygen may be accomplished by the use of a peroxide material which, upon decomposition, provides active oxygen for metabolic use.

It is also the case that there are vitamins, minerals and enzymes which if admixed and metabolized together by the human body tend to reduce the efficiency of one or both of the materials. While joint presence does not normally present a health hazard, joint presence may contribute to reduced potency of one or the other of the other materials present in the mixture.

Moreover, it is well known that certain materials tend to potentiate the action of other materials and are thus used in combinations. It is thus an object of this invention to provide a product which includes processed bovine colostrum, magnesium peroxide, vitamin C, bioflavonoids, magnesium succinate and which may be consumed by humans with beneficial effects. It is also an object of the present invention to provide an improved ingestable supplement product such as vitamin, mineral, enzyme, body cleansing, immune system enhancers and cholesterol reducing supplements.

It is another object of this invention to provide an ingestable product of the type described which contains powdered colostrum and a solid activated oxygen in addition to vitamins, minerals., enzymes and other beneficial materials.

Yet another object of this invention is to provide a ingestable product of the type described which contains solid processed bovine colostrum and stable solid activated oxygen material, the latter in the form of a peroxide, each of which is available from commercial suppliers, thus permitting compounding of the various products with relative ease.

Still another object of the present invention is the provision of an ingestable supplement product of the type described containing both processed solid colostrum and solid stable activated oxygen in the form of a peroxide wherein the product has a relatively long shelf life and wherein the various metabolically incompatible components are contained in one pill or capsule and wherein the incompatible materials are separated from each other for staged separate release and sequential absorption into the body.

It is yet another object of this invention to provide a product of the type described, for oral ingestion, which contains solid stable activated oxygen in the form of a mineral peroxide and solid processed colostrum and wherein the activated oxygen enhances the bacteriostatic and other desirable qualities of the colostrum.

BRIEF DESCRIPTION OF THE INVENTION

The above and other objects of this invention are achieved by a synergistic combination of a processed bovine colostrum and a mineral peroxide, the latter providing not only a mineral needed by the human body but also active oxygen.

It is preferred, in accordance with this invention, that the product include colostrum so that the antimicrobial, antibacteriostatic and immunological effects of the colostrum are enhanced by the stable activated oxygen. It is also the case that the presence of stable activated oxygen separately provides oxygen needed for the blood. In general, colostrum is present in an amount of at least 0.05% and as much as 5% by weight of the complete composition, with the preferred amount being of the order of 1% by weight of the composition. In one form of composition of this invention, the processed bovine colostrum may be present in an amount of up to 25% by weight. A suitable commercial source of colostrum is a food grade bovine colostrum available from Immuno-Dynamics, Inc., of Perry, Iowa. Typically, the colostrum is gathered from certified healthy cattle within 24 hours after the birth of the second calf. The gathered colostrum is frozen for transportation to a USDA approved processing plant. At the plant, it may be filtered for impurities, pasteurized, homogenized and gently spray dried at relatively low temperature to assure retention of biological activity. Typically, the processed bovine colostrum product is a light tan fluffy powder, soluble in water and having a slightly toasty odor. As supplied, it contains about 5% water and not less than 55% protein with 27% being immunoglobulins; fat is present in an amount not to exceed 14%. The term "processed colostrum" thus refers to the natural and preferably bovine colostrum which has been processed by reputable processors. A list of such processors is available from the Center for Bovine Colostrum Research located in Salt Lake City, Utah.

Since the processing of natural bovine colostrum to produce a biologically active product, as above described, involves pasteurization which may result in dehydration of the enzymes present in natural colostrum with the result that the bacteriostatic character of processed biologically active colostrum is somewhat less than the native colostrum since the hydrogen peroxide forming enzymes, one source of active oxygen, have been removed or rendered at least partially inactive.

In accordance with this invention, the reduced content of hydrogen peroxide forming enzymes and thus the oxidizing character of the biologically active colostrum is compensated for by the use of an effective amount of stable activated oxygen. The result is that the final product contains the immunoglobulins and proteins of the processed bovine colostrum and the activated oxygen, preferably present as magnesium peroxide, which promotes the antimicrobial quality of the product as well as providing a needed mineral and oxygen for use in the metabolic functions of the body.

In one form, the material of this invention includes as active ingredients the processed colostrum, magnesium peroxide as well as bioflavonoids, vitamin C and magnesium succinate, this mixture being referred to as the colostrum component. The bioflavonoids cooperate with the vitamin C to promote metabolism thereof while the succinate promotes metabolism of the magnesium of the magnesium peroxide. The above materials, i.e., the colostrum component, may also be used to provide an outer layer of a wide variety of capsules or tablets whose interior components may vary widely.

For example, the inner core component may be any one of herbs, minerals, amino acids, phytochemicals, vitamins, enzymes and high energy complexes for nutrition, or mixtures of the above. Other materials which may be present in the inner core to form yet other products include anti-acids, specific enzymes to assist digestion, as well as carbohydrate formulations to enhance athletic (aerobic) performance. Various classes of products in accordance with this invention include immune system building compositions which reduce the effects of free-radicals and which are believed to be the cause of some diseases and which contribute to the aging process. Other classes of products include (a) vitamin and mineral supplements to promote overall wellness and maintain balanced health, (b) enzyme supplements which promote metabolizing of vitamins and minerals, (c) cholesterol fighting supplements which may contain the Omega group of fatty acids which are believed to minimize cholesterol in the blood stream, (d) herb and high energy supplements, and (e) body cleansing supplements which assist the body in fighting off pathogenic bacteria, parasites, yeast and the like. It will be apparent from the following description that the colostrum component may be consumed as a separate supplement with all of the advantages arising from the components thereof. It is also the case that the colostrum component may be intimately admixed with other materials such as vitamins, minerals, enzymes and mixtures thereof and the like, in which event the benefits of the colostrum component and the additional additives are achieved. On special advantage of this invention is that the colostrum component may be used as an outer shell to encapsulate an inner core which may contain materials which are incompatible with one or more materials of the colostrum component. In this way, one pill, capsule or tablet may be used form incompatible materials, which may be taken in one pill and sequentially released for metabolic consumption by the body.

While the specification concludes with claims particularly pointing out and distinctly claiming the subject matter which is regarded as the invention, it is believed that the invention, the objects and features of the invention, and further objects, features and advantages thereof will be better understood from the following detailed description, it being understood that the same is illustrative of the invention and should not be construed in a limiting sense.

DETAILED DESCRIPTION OF THE INVENTION

A wide variety of products for ingestion by human beings, in accordance with this invention include, in one form, processed bovine colostrum, a mineral peroxide such as magnesium peroxide, vitamin C and a mineral succinate of the same mineral as the peroxide, for example, magnesium peroxide and one or more bioflavonoids. Preferably, each of the colostrum, peroxide and bioflavonoids, vitamin are present in the range of 20% to 30% by weight while the succinate is present in a lesser amount, e.g., 5 to 10%. It is also the case that the amount of materials such as vitamins and minerals which have an established minimum daily nutritional requirement, as established by the Food and Drug Administration, may be present in an amount of from at least 2% of the minimum daily requirement (MDR) to a multiple of the minimum daily requirement. One typical formulation is as follows:

| Material | Amount | MDR |
| --- | --- | --- |
| Processed bovine colostrum | 100 mg | NE |
| Magnesium peroxide | 100 mg | NE |
| (magnesium from peroxide) | 44 mg | 10.2 |
| (oxygen from the peroxide) | 56 mg | NE |
| Magnesium succinate | 30 mg | |
| Vitamin C | 100 mg | 166 |
| Bioflavonoids complex | 100 mg | NE |

The designation "NE" indicates that no minimum daily dietary amount has been established. The numerical values represent the percentage of the minimum daily requirement. Another typical formulation is as follows:

| Material | Amount | NDR |
| --- | --- | --- |
| Processed bovine colostrum | 100 mg | NE |
| Magnesium peroxide | 250 mg | NE |
| (magnesium from peroxide) | 107 mg | 26.8 |
| (oxygen from the peroxide) | 143 mg | NE |
| Magnesium succinate | 30 mg | |
| Vitamin C | 200 mg | 166 |
| Bioflavonoid complex | 100 mg | NE |

The materials of the above two examples may be taken as an ingestable supplement to provide effective amounts of vitamin C and colostrum and active oxygen. Such a supplement, in a pill or capsule or other ingestable form provides the benefits of both colostrum and active oxygen as well as the benefits of the mineral and vitamin components. The magnesium peroxide is a source both of amounts indicated. One n the amounts indicated. One suitable source of the magnesium peroxide is Hummel Croton Inc., 10 Hamrich Road South, Plainfield, N.J. 07080.

As mentioned, the colostrum product of the above examples may be taken orally as a colostrum supplement with all of the attendant benefits, or it may be admixed with compatible minerals, vitamins or enzymes, and the like, or it may be used as the outer shell of a multilayered pill or capsule to separate, temporarily, possible incompatible materials. In accordance with this preferred form of the present invention, the colostrum materials are used to form the outer shell of a pill or tablet whose inner core may be any one of a variety of mixtures depending upon the overall intended function of the pill or tablet. Many of the various core types have already been mentioned.

In operation, the outer shell is dissolved first upon consumption of the pill and metabolized by the body followed by dissolution and assimilation of the components of the inner core.

The following are several examples of a variety of composite pills and tablets in accordance with this aspect of the invention.

| Material | Amount | MDR |
| --- | --- | --- |
| Processed bovine colostrum | 100 mg | NE |
| Magnesium peroxide | 100 mg | NE |
| (magnesium from peroxide) | 44 mg | 10.2 |
| (oxygen from the peroxide) | 56 mg | NE |
| Magnesium succinate | 30 mg | |
| Vitamin C | 100 mg | 166 |
| Bioflavonoids complex | 100 mg | NE |

The above materials form the outer shell while the inner core includes the following materials in the amounts indicated.

| | | |
| --- | --- | --- |
| Vitamin A | 3,500IU | 70 |
| Vitamin E | 150IU | 500 |
| Vitamin B1 (Thiamine) | 2 mg | 133 |
| Vitamin B2 (Riboflavin) | 2 mg | 118 |
| Vitamin B3 (Niacin) | 12 mg | 60 |
| Vitamin B5 (Panthothenic acid) | 12 mg | 120 |
| Vitamin B12 (Cyanocobalamin) | 24 mcg | 400 |
| Calcium | 50 mg | 5 |
| Selenium | 10 mcg | NE |
| Iron | 10 mg | 55 |
| Grape Seed Extract | 7 mg | NE |
| Red Wine Extract | 2 mg | NE |
| Ginko Biloba | 10 mg | NE |
| Gensing | 10 mg | NE |
| CoEnzyme Q10 | 2.5 mg | NE |
| Green Tea | 65 mg | NE |
| Garlic | 150 mg | NE |
| Lycopene | 18 mcg | NE |
| Quercetin | 10 mg | NE |
| Milk Thistle Extract | 10 mg | NE |
| Biotin | 200 mcg | NE |
| Bilberry | 8 mg | NE |
| N-Acetylcysteine | 8 mg | NE |
| Inositol hexanicotinate | 3 mg | NE |
| Parsley | 3 mg | NE |
| Chlorophyll (Chlorella) | 3 mg | NE |
| Glutathione | 3 mg | NE |
| Lipase | 3 mg | NE |
| Amylase | 3 mg | NE |
| Cellulase | 3 mg | NE |
| Kelp | 3 mg | NE |

The above example is an immune system tablet and contains ingredients to fight off free-radicals which are believed to cause many diseases as well as being at the heart of the aging process.

The following example is for a vitamin and mineral supplement.

| Material | Amount | MDR |
| --- | --- | --- |
| Processed bovine colostrum | 100 mg | NE |
| Magnesium peroxide | 100 mg | NE |
| (magnesium from peroxide) | 44 mg | 10.2 |
| (oxygen from the peroxide) | 56 mg | NE |
| Magnesium succinate | 30 mg | |
| Vitamin C | 100 mg | 166 |
| Bioflavonoids complex | 100 mg | NE |

The above materials form the outer shell while the inner core includes the following materials in the amounts indicated.

| | | |
| --- | --- | --- |
| Vitamin A | 800IU | 16 |
| Vitamin B1 (Thiamine) | 5 mg | 333 |
| Vitamin B2 (Riboflavin) | 5 mg | 294 |
| Vitamin B3 (Niacin) | 15 mg | 75 |
| Vitamin B5 (Panthothenic acid) | 15 mg | 150 |
| Vitamin B6 (Pridoxine hydrochloride) | 3 mg | NE |
| Vitamin D | 75IU | 18.8 |
| Vitamin E | 30 mg | 100 |
| Vitamin K | 150 mcg | NE |
| Folate (folic acid) | 150 mcg | 37.5 |
| Biotin | 200 mcg | 66.7 |
| Calcium | 150 mg | 15 |
| Iodine (from kelp) | 15 mcg | 16.7 |
| Iron | 20 mg | 111 |
| Zinc | 10 mg | 66.6 |
| Selenium | 10 mcg | NE |
| Copper | 300 mcg | 15 |
| Manganese | 1.5 mg | NE |
| Phosphorus | 20 mg | 2 |
| Chromium | 65 mg | NE |
| Molybdenum | 35 mg | NE |
| Potassium | 20 mg | NE |
| Boron | 150 mcg | NE |
| Vanadium | 10 mcg | NE |
| Choline | 35 mg | NE |
| Inositol | 18 mg | NE |
| PAPA | 5 mg | NE |
| Silicon | 5 mg | NE |
| Lipase | 3 mg | NE |
| Amylase | 3 mg | NE |
| Cellulase | 3 mg | NE |
| Kelp | 3 mg | NE |

The vitamin and mineral supplement of the preceding example is intended to enhance overall wellness and provide to the body the essential and trace minerals needed to ward off diseases and to maintain balanced health.

The following example is of a product which contains a combination of enzymes.

| Material | Amount | MDR |
| --- | --- | --- |
| Processed bovine colostrum | 100 mg | NE |
| Magnesium peroxide | 100 mg | NE |
| (magnesium from peroxide) | 44 mg | 10.2 |
| (oxygen from the peroxide) | 56 mg | NE |
| Magnesium succinate | 30 mg | |

-continued

| Material | Amount | MDR |
| --- | --- | --- |
| Vitamin C | 100 mg | 166 |
| Bioflavonoids complex | 100 mg | NE |

The above materials form the outer shell while the inner core includes the following materials in the amounts indicated.

| | | |
| --- | --- | --- |
| Amylase | 10,000IU | NE |
| Protease | 20,000HUT | NE |
| Invertase | 0.5IAU | NE |
| Lipase | 100IU | NE |
| Maltase | 200DP | NE |
| Cellulase | 200CU | NE |
| Lactase | 100LacU | NE |

Enzymes are important in metabolizing vitamins and minerals.

The following is an example of a cholesterol fighting supplement which includes a combination of omega fatty acids.

| Material | Amount | MDR |
| --- | --- | --- |
| Processed bovine colostrum | 100 mg | NE |
| Magnesium peroxide | 100 mg | NE |
| (magnesium from peroxide) | 44 mg | 10.2 |
| (oxygen from the peroxide) | 56 mg | NE |
| Magnesium succinate | 30 mg | |
| Vitamin C | 100 mg | 166 |
| Bioflavonoids complex | 100 mg | NE |

The above materials form the outer shell while the inner core includes the following materials in the amounts indicated.

| | | |
| --- | --- | --- |
| Omega-3 fatty acids | 600 mg | NE |
| Omega-6 fatty acids | 200 mg | NE |
| Omega-9 fatty acids | 200 mg | NE |

Omega fatty acids cannot be synthesized by the body and cholesterol is believed to be minimized in the blood stream when adequate supplies of Omega acids are present in the blood stream.

An example of an herb and mineral supplement in accordance with this invention is as follows:

| Material | Amount | MDR |
| --- | --- | --- |
| Processed bovine colostrum | 100 mg | NE |
| Magnesium peroxide | 100 mg | NE |
| (magnesium from peroxide) | 44 mg | 10.2 |
| (oxygen from the peroxide) | 56 mg | NE |
| Magnesium succinate | 30 mg | |
| Vitamin C | 100 mg | 166 |
| Bioflavonoids complex | 100 mg | NE |

The above materials form the outer shell while the inner core includes the following materials in the amounts indicated.

| | | |
| --- | --- | --- |
| *Hydrilla verticicillata* | 100 mg | NE |
| Wheat grass juice powder | 70 mg | NE |
| Barley grass juice powder | 70 mg | NE |
| Broccoli Phytochemicals | 40 mg | NE |
| Cauliflower | 40 mg | NE |
| Blue-green algae | 40 mg | NE |

-continued

| | | |
| --- | --- | --- |
| Celery seed powder | 20 mg | NE |
| Parsley powder | 20 mg | NE |
| Carrot powder | 20 mg | NE |
| Royal jelly | 20 mg | NE |
| Tumeric | 20 mg | NE |
| Cats claw | 20 mg | NE |
| Siberian ginseng | 10 mg | NE |
| Korean ginseng | 10 mg | NE |
| American ginseng | 10 mg | NE |
| Reishi mushroom | 10 mg | NE |
| Shitake mushroom | 10 mg | NE |
| Fo Ti | 10 mg | NE |
| Austragalus | 10 mg | NE |
| Hawthorne | 10 mg | NE |
| Dong Kola | 10 mg | NE |
| Gota Kola | 10 mg | NE |
| Suma | 10 mg | NE |
| Wild oat extract | 10 mg | NE |
| Ginger | 10 mg | NE |
| Cayenne | 10 mg | NE |
| Licorice | 10 mg | NE |
| Rosemary | 5 mg | NE |
| Oregano | 5 mg | NE |
| Sage | 5 mg | NE |
| Thyme | 5 mg | NE |
| Octacosanol | 5 mg | NE |
| Lipase | 3 mg | NE |
| Amylase | 3 mg | NE |
| Cellulase | 3 mg | NE |
| Kelp | 3 mg | NE |

Many raw fruits, vegetables and herbs contain metabolic enhancing components known as phytochemicals. The phytochemicals work with vitamins, minerals, proteins and fatty acids and enzymes to enhance metabolic function and cellular activity.

The following is an example of a body conditioner and cleansing supplement in accordance with this invention.

| Material | Amount | MDR |
| --- | --- | --- |
| Processed bovine colostrum | 100 mg | NE |
| Magnesium peroxide | 250 mg | NE |
| (magnesium from peroxide) | 107 mg | 26.8 |
| (oxygen from the peroxide) | 143 mg | NE |
| Magnesium succinate | 30 mg | |
| Vitamin C | 200 mg | 166 |
| Bioflavonoid complex | 100 mg | NE |

The above materials form the outer shell while the inner core includes the following materials in the amounts indicated.

| | | |
| --- | --- | --- |
| Calcium | 100 mg | 100 |
| Potassium | 100 mg | NE |
| Vitamin B1 (Thamine) | 10 mg | 666 |
| Vitamin B2 (Riboflavin) | 10 mg | 588 |
| Vitamin B6 | 10 mg | 500 |
| Vitamin B12 | 24 mg | 400 |
| Vitamin F | 60IU | 200 |
| Magnesium | 50 mg | 12.5 |
| Fibrosol (natural fiber) | 150 meg | NE |

Magnesium in combination with oxygen deodorizes the lower digestive system and helps the body fight off pathogenic bacteria, parasites, yeasts, and the like, that may reside in the digestive tract. The remaining ingredients help boost the immune system as the body goes through the cleansing cycle.

It is apparent from the above detailed description that processed bovine colostrum and a stable source of oxygen in the form of magnesium peroxide, along with other materials such as vitamin C and magnesium succinate and the bioflavonoids provide a powerful supplement for the human body. The colostrum and vitamin C boost the immune system's ability to ward off disease, while magnesium provides the body cells with a key ingredient for cellular metabolism. The bioflavonoids are present to facilitate the utilization of vitamin C while the magnesium succinate is used to allow the utilization of magnesium by the body. With these basic qualities of the principal ingredients of the basic composition, as described, a wide variety of other materials may be added in various amounts, known in the art, to provide added supplemental benefits.

The procedure for making the core and the outer shell, where a shell and core structure are used are well known in the art, as are the procedures for forming pills, capsules or tablets.

The colostrum group of ingredients may be used to isolate added components by forming an outer shell that separates those components that are incompatible with the components of the shell material by forming pills or tablets having an inner core and outer shell. It is also the case that such separation It is contemplated that numerous changes, modifications and/or additions may be made to the specific embodiments of the present invention described in the detailed description without departing from the spirit and scope of the present invention. Accordingly, it is intended that the scope of this patent be limited only by the scope of the appended claims and equivalents thereof.

What is claimed is:

1. An ingestable supplement for human consumption comprising effective concentrations of:

a colostrum product containing not less than 55% protein with fat present in an amount not to exceed 14%, a mineral peroxide, a bioflavonoid, vitamin C, and a mineral succinate of the same mineral as said peroxide.

2. An ingestable supplement as set forth in claim 1 including an inner core and wherein the colostrum product forms an outer shell encapsulating the core.

3. An ingestable supplement as set forth in claim 1 wherein said mineral peroxide is magnesium peroxide and wherein said succinate is magnesium succinate.

4. An ingestable supplement as set forth in claim 3 wherein said magnesium peroxide, bioflavonoids, vitamin C and said colostrum product are each present in an amount of between 20% and 30% by weight.

5. An ingestable supplement in claim 2 wherein said core includes Omega acids.

6. An ingestable supplement in claim 2 wherein said core includes at least one vitamin.

7. An ingestable supplement in claim 2 wherein said core includes at least two enzymes.

8. An ingestable supplement in claim 2 wherein said core includes at least two herbs.

9. An ingestable supplement in claim 2 wherein said core includes at least two minerals.

10. An ingestable supplement as set forth in claim 2 wherein said core includes natural fiber.

* * * * *